United States Patent [19]

Kaminski

[11] Patent Number: 5,352,688
[45] Date of Patent: Oct. 4, 1994

[54] METHODS FOR THE TREATMENT OF BRADYPHRENIA IN PARKINSON'S DISEASE

[75] Inventor: Ram Kaminski, Riverdale, N.Y.

[73] Assignee: The Mount Sinai School of Medicine of the City University of New York, New York, N.Y.

[21] Appl. No.: 954,258

[22] Filed: Sep. 30, 1992

Related U.S. Application Data

[60] Continuation-in-part of Ser. No. 743,254, Aug. 9, 1991, Pat. No. 5,177,081, which is a division of Ser. No. 655,759, Feb. 15, 1991, Pat. No. 5,070,101.

[51] Int. Cl.$^5$ ............... A61K 31/44; A61K 31/425; A61K 31/415; A61K 31/34
[52] U.S. Cl. ............... 514/357; 514/365; 514/370; 514/400; 514/471
[58] Field of Search ............... 514/370, 471, 400, 365, 514/357

[56] References Cited

U.S. PATENT DOCUMENTS 4,757,060  4/1986  Lukacsko et al. ............... 514/140

OTHER PUBLICATIONS

Berkow et al., 1982, "The Merck Manual of Diagnosis and Therapy", 14th Edition, published by Merck, Sharp & Dohne Research Laboratories, pp. 1359–1362.
Kaminsky et al., *Effect of Famotidine on Deficit Symptoms of Schizophrenia*, The Lancet, vol. 335: pp. 1351–1352 (1990).
Alan J. Gelenberg, M.D., *Biological Therapies in Psychiatry Newsletter*, vol. 13, No. 11, (Nov. 1990).
*Drug Information for the Health Care Professional*, USP DI 1990 10th Anniversary Edition, pp. 1495–1505 (1990).
Joseph R. Bianchine, *Drugs for Parkinson's Disease, Spasticity, and Acute Muscle Spasms*, MacMillan Publishing Company, Goodman and Gilman's The Pharmacological Basis of Therapeutics, Seventh Edition, Chapter 21: pp. 472–486, (1985).
E. L. Engelhardt and C. A. to Stone, *Antiparkinsonism Drugs*, Medicinal Chemistry, Third Edition Part II: pp. 1537–1543 (1985).
J. H. Growdon, S. Corkin, and T. J. Rosen, *Distinctive Aspects of Cognitive Dysfunction in Parkinson's Disease*, Advances in Neurology, vol. 53: pp. 365–37, Parkinson's Disease; Anatomy, Pathology, and Therapy (1990).
W. Danilczyk and P. Fischer, *Psychiatric complications and Shift of Death Age in Parkinson's Disease*, Advances in Neurology, vol. 53: pp. 405–410 Parkinson's Disease: Anatomy, Pathology, and Therapy (1990).
D. B. Calne and A. Eisen, *Parkinson's Disease, Motoneuron Disease and Alzheimer's Disease: Origins and Interrelationship*, Advances in Neurology, vol. 53: Parkinson's Disease: Anatomy, Pathology, and Therapy (1990).
Y. Agid et al., *The Efficacy of Levodopa Treatment Declines in the Course of Parkinson's Disease: Do Nondopaminergic Lesions Play a Role?*, Advances in Neurology, vol. 53: pp. 83–100 Parkinson's Disease: Anatomy, Pathology, and Therapy (1990).
J. L. Cummings, M.D., *Depression and Parkinson's Disease: A Review*, Am. J. Psychiatry 149:4, pp. 443–454, (1992).

(List continued on next page.)

Primary Examiner—Gregory Hook
Attorney, Agent, or Firm—Brumbaugh, Graves, Donohue & Raymond

[57] ABSTRACT

Neuropsychiatric symptoms of Parkinson's Disease and particularly the symptoms of apathy-amotivation and mental slowing can be ameliorated by treating a patient suffering from Parkinson's Disease with a histamine H$_2$-antagonist that passes the blood brain barrier. Suitable H$_2$-antagonists include famotidine and ranitidine. The H$_2$-antagonists may be co-administered with other compounds such as histamine H,-antagonists which are known to be useful in the treatment of Parkinson's Disease, and can be formulated with such other compounds into a therapeutic composition.

14 Claims, No Drawings

OTHER PUBLICATIONS

M. Garbarg et al., *Brain Histidine Decarboxylase Activity in Parkinson's Disease,* The Lancet, 74–75, (1983).

M. H. Coelho et al., *Decrease in Blood Histamine in Drug-Treated Parkinsonian Patients,* Molecular and Chemical Neuropathology, vol. 14: pp. 77–85, (1991).

J. Poirier et al., *Debrisoquine Metabolism in Parkinsonian Patients Treated with Antihistamine Drugs,* The Lancet, p. 386, (1987).

S. Nakamura and S. Vincent, *Histochemistry of MPTP Oxidation in the Rat Brain: Sites of Synthesis of the Parkinsonism-Inducing Toxin MPP,* Neuroscience Letters, vol. 65: pp. 321–325, (1986).

Cumming et al., *Cerebral Histamine Levels are Unaffected by MPTP Administration in the Mouse,* European Journal of Pharmacology, vol. 166: pp. 299–301, (1989).

U. Knigge and J. Warberg, *The Role of Histamine in the Neuroendocrine Regulation of Pituitary Hormone Secretion,* Acta Endocrinologica (Copenh) vol. 124: pp. 609–619, (1991).

Cumming et al., *Cerebral Histamine Levels Are Unaffected By MPTP Administration In The Mouse,* European Journal of Pharmacology, vol. 184: pp. 299–301, (1990).

Oish et al., *Is Monoamine Turnover in the Brain Regulated by Histamine $H_3$ Receptors?,* European Journal of Pharmacology, vol. 184: pp. 135–142, (1990).

Cumming et al., *High Affinity Histamine Binding Site Is the $H_3$ Receptor: Characterization and Autoradiographic Localization in Rat Brain,* SYNAPSE 8, pp. 144–151 (1991).

S. Chiavegatto et al., *Effects of Prenatal Diphenhydramine Exposure on Dopaminergic Function in Adult Rats,* Pharmacology Biochemistry & Behavior, vol. 140: pp. 191–193, (1991).

Matzen et al., *Brain Regulation of Renin Secretion Involves Central Histaminergic Neurons,* Neuroendocrinology, vol. 52: pp. 175–180, (1990).

Sakai et al., *Effects of Thioperamide, A Histamine $H_3$ Receptor Antagonist, on Locomotor Activity and Brain Histamine Content in Mast Cell-Deficient W/W Mice,* Life Sciences, vol. 48: pp. 2397–2404 (1991).

Onodera et al., *Pharmacological Characteristics of Catalepsy Induced by Intracerebroventricular Administration of Histamine in Mice: The Importance of Muscarinic Step in Central Cholinergic Neurons,* Birkhäuser Verlag, Basel, Agents and Actions, vol. 33: pp. 143–146, (1991).

U. P. Knigge, *Histaminergic Regulation of Prolactin Secretion,* vol. 37, No. 2: pp. 109–124, (1990).

A. Eisen and D. Calne, *Amyotrophic Lateral Sclerosis, Parkinson's Disease and Alzheimer's Disease: Phylogenetic Disorders of the Human Neocortex Sharing Many Characteristics,* Can. J. Neurol. Sci., vol. 19: pp. 117–120, (1992).

Dooneief, M. D. et al., *An Estimate of the Incidence of Depression in Idiopathic Parkinson's Disease,* Arch Neurol, vol. 49, (Mar. 1992).

M. H. Sharpe, *Auditory Attention in Early Parkinson's Disease: An Impairment in Focused Attention,* Neuropsychologica, vol. 30, No. 1: pp. 101–106 (1992).

METHODS FOR THE TREATMENT OF BRADYPHRENIA IN PARKINSON'S DISEASE

This application is a continuation-in-part of prior application, Ser. No. 07/743,254, filed Aug. 9, 1991, which is a divisional of application Ser. No. 655,759, filed Feb. 15, 1991, now U.S. Pat. No. 5,070,101. The disclosure of U.S. Pat. No. 5,070,101 is incorporated herein by reference.

BACKGROUND OF THE INVENTION

This application relates to a method and composition for use in the treatment of Parkinson's Disease.

Parkinson's Disease was first described in 1817 by James Parkinson in a paper entitled "An Essay on the Shaking Palsy". Since then, it has become increasingly clear that Parkinson's Disease involves a complex cluster of symptoms which respond differently to therapeutic treatments.

These symptoms can be classified into two groups: those manifesting themselves as motor dysfunction, and those which can be characterized as neuropsychiatric disorders or symptoms. In the latter group there are three recognized components, (1) apathy-amotivation; (2) depression and (3) dementia.

The motor dysfunction symptoms of Parkinson's Disease have been treated in the past using dopamine, receptor agonists, monoamine oxidase binding inhibitors, anticholinergics and histamine $H_1$-antagonists, although it is probable that it is the anticholinergic rather than the antihistamine activity of the latter group which is responsible for therapeutic effects. These treatments have little or no benefit with respect to the neuropsychiatric symptoms.

It is an object of the present invention to provide a treatment for the neuropsychiatric symptoms of Parkinson's Disease.

SUMMARY OF THE INVENTION

In accordance with the present invention, neuropsychiatric symptoms of Parkinson's Disease and particularly the symptoms of apathy-amotivation and mental slowing can be ameliorated by treating a patient suffering from Parkinson's Disease with a histamine $H_2$-antagonist that passes the blood brain barrier. Suitable $H_2$-antagonists include famotidine and ranitidine.

The $H_2$-antagonists may be co-administered with other compounds which are known to be useful in the treatment of Parkinson's Disease, and in one aspect of the invention can be formulated with such other compounds into a therapeutic composition.

DETAILED DESCRIPTION OF THE INVENTION

The claimed invention relates to treatment of the apathy-amotivation and mental slowing observed in Parkinson's patients. These symptoms have been referred to as bradyphrenia, psychic akinesia or subcortical dementia. The term "bradyphrenia" will be used in the specification and claims hereof to refer to these symptoms.

Bradyphrenia is similar in its manifestation to the negative symptoms of schizophrenia and the pathophysiology may be related, although there is no indication that the etiology of these symptoms are the same. Nevertheless, these symptoms respond to the same therapy which I found to be effective for treating schizophrenia.

Thus, bradyphrenia is treated in accordance with the invention by administering a histamine $H_2$-antagonist that passes the blood-brain barrier to the patient. Suitable histamine $H_2$-antagonists include famotidine, ranitidine, cimetidine, nizatidine, omeprazole, tiotidine and aminofurazan compounds.

The preferred mode of administration is oral administration. Preparations for oral administration can be formulated in various forms (e.g. liquid, tablets, capsules) and may include appropriate excipients, flavorants, colorants and other carrier materials. Other modes of administration, including intraperitoneal, intravenous and intramuscular administration can be employed, however, particularly if the patient is uncooperative.

In addition to the $H_2$-antagonist and appropriate carrier materials, the pharmaceutical preparation may include one or more therapeutic agents effective against symptoms of Parkinson's Disease other than bradyphrenia. Such materials include levodopa, carbidopa histamine $H_1$-antagonists (e.g. diphenhydramine), dopamine receptor agonists (e.g. apomorphines and ergotamines), anticholinergics (e.g. trihexyphenidyl), monoamine oxidase binding inhibitors (e.g. deprenyl), and compounds with combined actions (orphenadrine, chlorphenoxamine and benztropine).

Histamine $H_2$-antagonists are administered in amounts sufficient to ameliorate the symptoms of bradyphrenia. For example, $H_2$-antagonists are suitably administered in amounts of 20–600 mg/day, although the upper limit is imposed by a concern over side effects rather than a loss of efficacy. Preferably, the $H_2$-antagonist is administered in an amount of from 80–160 mg/day. Pharmaceutical compositions in accordance with the invention are prepared to deliver the effective amount of $H_2$-antagonist in view of the anticipated frequency of treatment.

While not intending to be bound to a particular theory, the efficacy of histamine $H_2$-antagonists in the treatment of neuropsychiatric symptoms of Parkinson's disease is believed to result from a reversal of the effects of elevated histamine levels on the $H_2$ receptors of the brain to increase the level of arousal and motivated behavior. This theory is consistent with the observation of elevated blood histamine levels in untreated Parkinson's patients. Coelho et al., Molecular & Chemical Neuropathology 14, 77–85 (1991). It is also consistent with the observation that $H_2$-receptors in the brain are predominantly localized in the same portions of the brain, i.e., the caudate putamen and the globus pallidus, that are implicated in the pathophysiology of Parkinson's disease, Martinez-Mir et al., Brain Research 526, 322–327 (1990); and the hypothesis that hyperactive histamine neurons resulting from a dopamine deficiency may be involved in Parkinson's disease. Garbarg et al., The Lancet 1, 74–75 (1983). Nevertheless, no association between histamine and the neuropsychiatric symptoms of Parkinson's Disease has been suggested prior to this invention.

I claim:

1. A method for treating the symptoms of bradyphrenia in a patient suffering from Parkinson's Disease comprising administering to the patient a compound selected from the group consisting of famotidine, ranitidine, cimetidine, nizatidine, omeprazole, tiotidine, and aminofurazan compounds, that crosses the blood brain barrier in an amount effective to ameliorate the symptoms of bradyphrenia.

2. A method for treating the symptoms of bradyphrenia in a patient suffering from Parkinson's Disease comprising administering to the patient a compound selected from the group consisting of famotidine, ranitidine and cimetidine that crosses the blood brain barrier in an amount effective to ameliorate the symptoms of bradyphrenia.

3. A method for treating the symptoms of bradyphrenia in a patient suffering from Parkinson's Disease comprising administering to the patient a compound selected from the group consisting of famotidine, famotidine homologs and famotidine isomers that crosses the blood brain barrier in an amount effective to ameliorate the symptoms of bradyphrenia.

4. A method according to claim 1, 2 or 3 wherein the compound is administered in an amount of from 20 to 600 mg/day.

5. A method according to claim 4 wherein the compound is administered in an amount from 80 to 160 mg/day.

6. A method according to claim 1, 2 or 3 wherein the compound is famotidine.

7. A method according to claim 6, wherein the compound is administered in an amount of from 20 to 600 mg/day.

8. A method according to claim 7 wherein the compound is administered in an amount of from 80 to 160 mg/day.

9. A method according to claim 1 or 2, wherein the compound is ranitidine.

10. A method according to claim 1, 2 or 3 further comprising co-administering an additional therapeutic agent effective against symptoms of Parkinson's Disease other than bradyphrenia.

11. A method according to claim 10, wherein the additional therapeutic agent is a dopamine receptor agonist.

12. A method according to claim 10, wherein the additional therapeutic agent is a histamine $H_1$-antagonist.

13. A method according to claim 10, wherein the compound is famotidine.

14. A method according to claim 10, wherein the compound is ranitidine.

* * * * *